US00PP12245P2

(12) United States Plant Patent
Wakaiki

(10) Patent No.: US PP12,245 P2
(45) Date of Patent: Dec. 4, 2001

(54) *CAMPSIS RADICANS* NAMED 'TAKARAZUKA VARIEGATED'

(75) Inventor: Shinri Wakaiki, Takarazuka (JP)

(73) Assignee: Hines Nurseries, Inc., Irvine, CA (US)

( * ) Notice: Subject to any disclaimer, the term of this patent is extended or adjusted under 35 U.S.C. 154(b) by 0 days.

(21) Appl. No.: 09/411,662

(22) Filed: Oct. 4, 1999

(51) Int. Cl.[7] ..... A01H 5/00

(52) U.S. Cl. ..... Plt./226

(58) Field of Search ..... Plt./226

*Primary Examiner*—Bruce R. Campell
*Assistant Examiner*—June Hwu
(74) *Attorney, Agent, or Firm*—Christie, Parker & Hale, LLP

(57) ABSTRACT

A new plant variety of *Campsis radicans* characterized by its flecked and mottled white variegated foliage, which is exhibited from the emergence of the foliage through maturity.

5 Drawing Sheets

BACKGROUND OF THE INVENTION

The present invention relates to a new and distinct variety of *Campsis radicans* and was discovered as a branch sport in a controlled planting of *Campsis radicans* in Sakaino, Takarazuka City, Japan. The varietal denomination of the new variety is 'TAKARAZUKA VARIEGATED'.

The genus Campsis is included in the family Bignoniaceae which comprises about 110 genera and 750 species of trees, shrubs, woody vines growing in the northern and southern hemispheres. The genus Campsis comprises 2 species, one native to North America and the other to East Asia, of deciduous shrubs climbing by aerial rootlets. In the landscape it can be used as a vine, both species possess desirable ornamental characteristics.

*Campsis radicans* (Linnaeus) B.C. Seemmann ex. Bureau is widespread and common throughout much of the Eastern United States from Pennsylvania to Missouri, Florida and Texas. It generally has opposite, odd-pinnately compound leaves about 15 to 40 cm long, about 2 to 10 cm wide, with an acuminate apex, lustrous dark green above and glabrous, pubescent beneath. The plant is deciduous. Flowers of *Camsis radicans* are perfect, with a wide-mouthed corolla, about 5 to 6 cm wide, borne 4 to 12 in terminal cymes from May until October. Flower color is yellow to orange to scarlet depending on the variety. The calyx teeth are short, triangular being much shorter than the flower tube. Of the varieties of *Campsis radicans* previously known to the inventor, all have green foliage ,and none exhibit variegated foliage.

SUMMARY OF THE INVENTION

The new variety was discovered as a branch sport in a controlled planting of *Campsis radicans* in Sakaino, Hyogo Prefecture, Japan, and differs from its parent and all other varieties of *Campsis radicans* known to the inventor in its flecked and mottled white variegated foliage, which is exhibited from the emergence of the foliage through maturity. Asexual reproduction of the new variety by stem cuttings performed in Sakaino Prefecture, Japan; Lewisberry, Pa.; Vacaville, Calif.; and Fulshear, Tex.; has confirmed that the distinctive characteristics of the new variety are stable and transmitted to succeeding generations, and the new vqariety reproduces true to type.

COMPARISON WITH PARENT

'TAKARAZUKA VARIEGATED' is distinguished from its parent and all other varieties of *Campsis radicans* of which I am aware by its flecked and mottled white variegated foliage, which is exhibited from the emergence of the foliage through maturity.

DESCRIPTION OF ILLUSTRATIONS

The accompanying photographic illustrations show a plant of the new cultivar as true to color as is reasonably possible to make in an illustration of this character.

DETAILED DESCRIPTION OF THE NEW VARIETY

Figure 1:
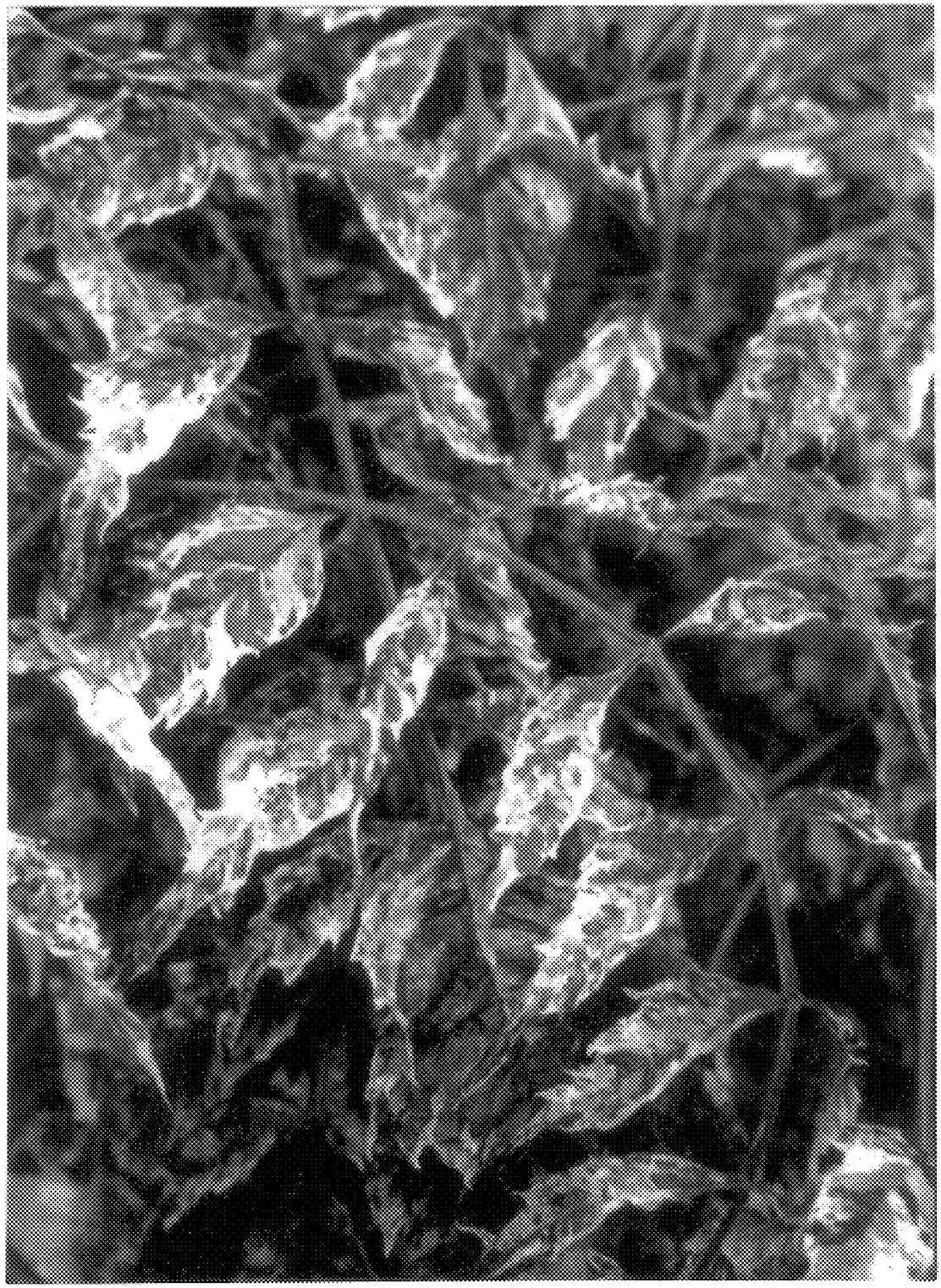
FIG. 1 illustrates the distinctive foliage variegation of a mature plant of the new variety.
Figure 2:
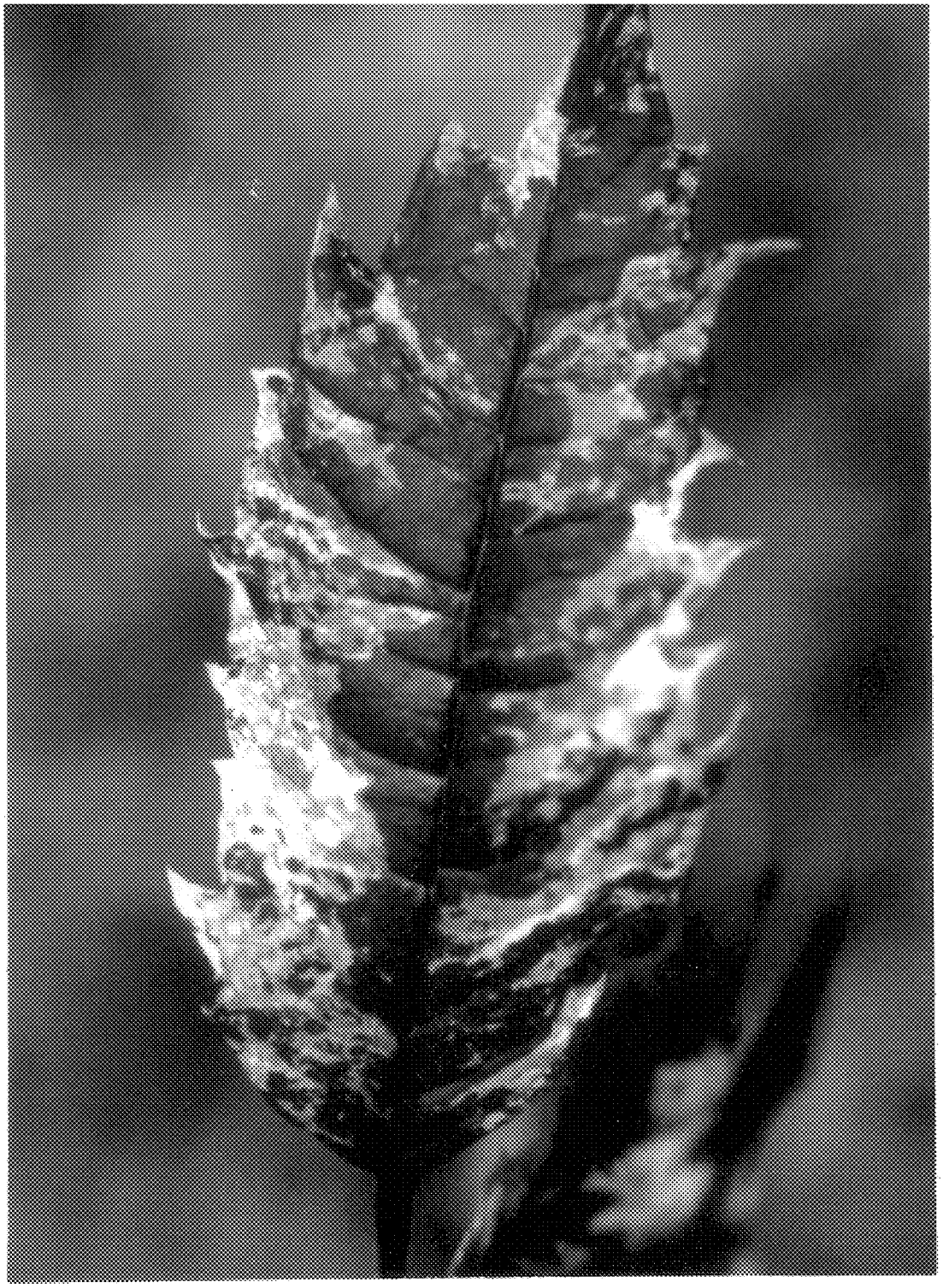
FIG. 2 illustrates a leaflet of the new variety which exhibits the distinctive foliage variegation.
Figure 3:
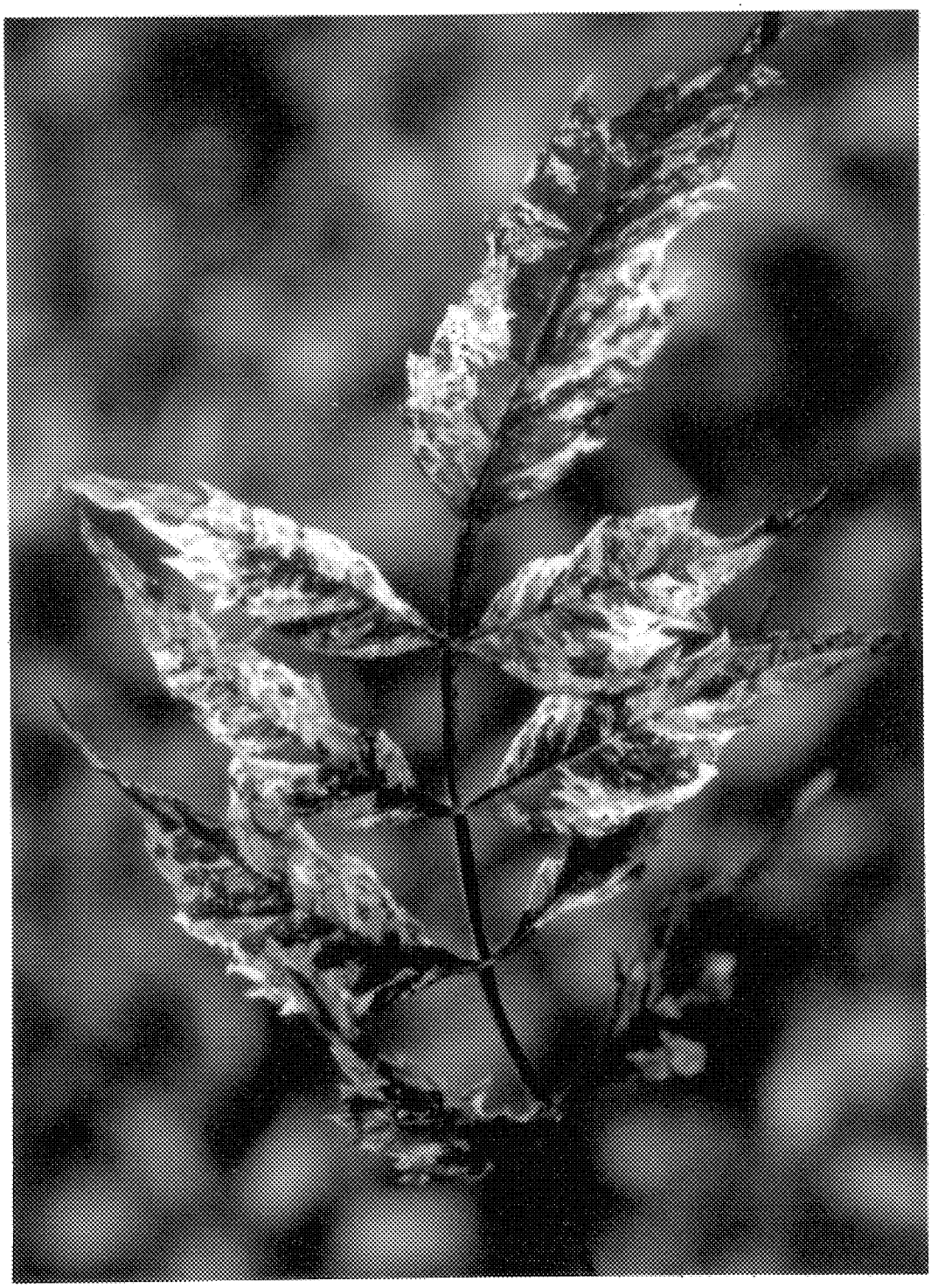
FIG. 3 illustrates an entire leaf of the new variety, which exhibits the distinctive foliage variegation.
Figure 4:
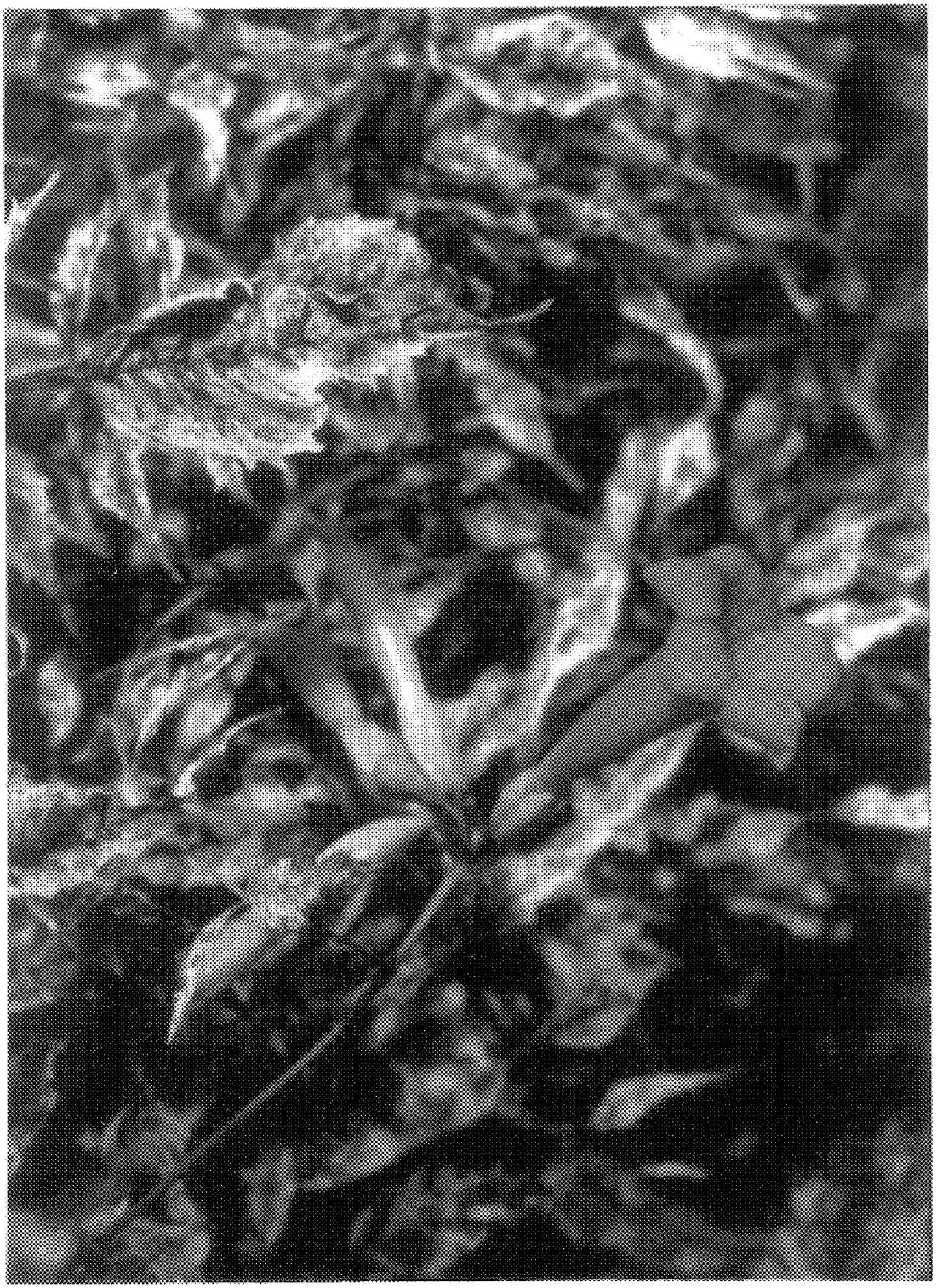
FIG. 4 illustrates the flower panicle; the calyx size and shape distinction of the new variety from other species of Campsis.
Figure 5:
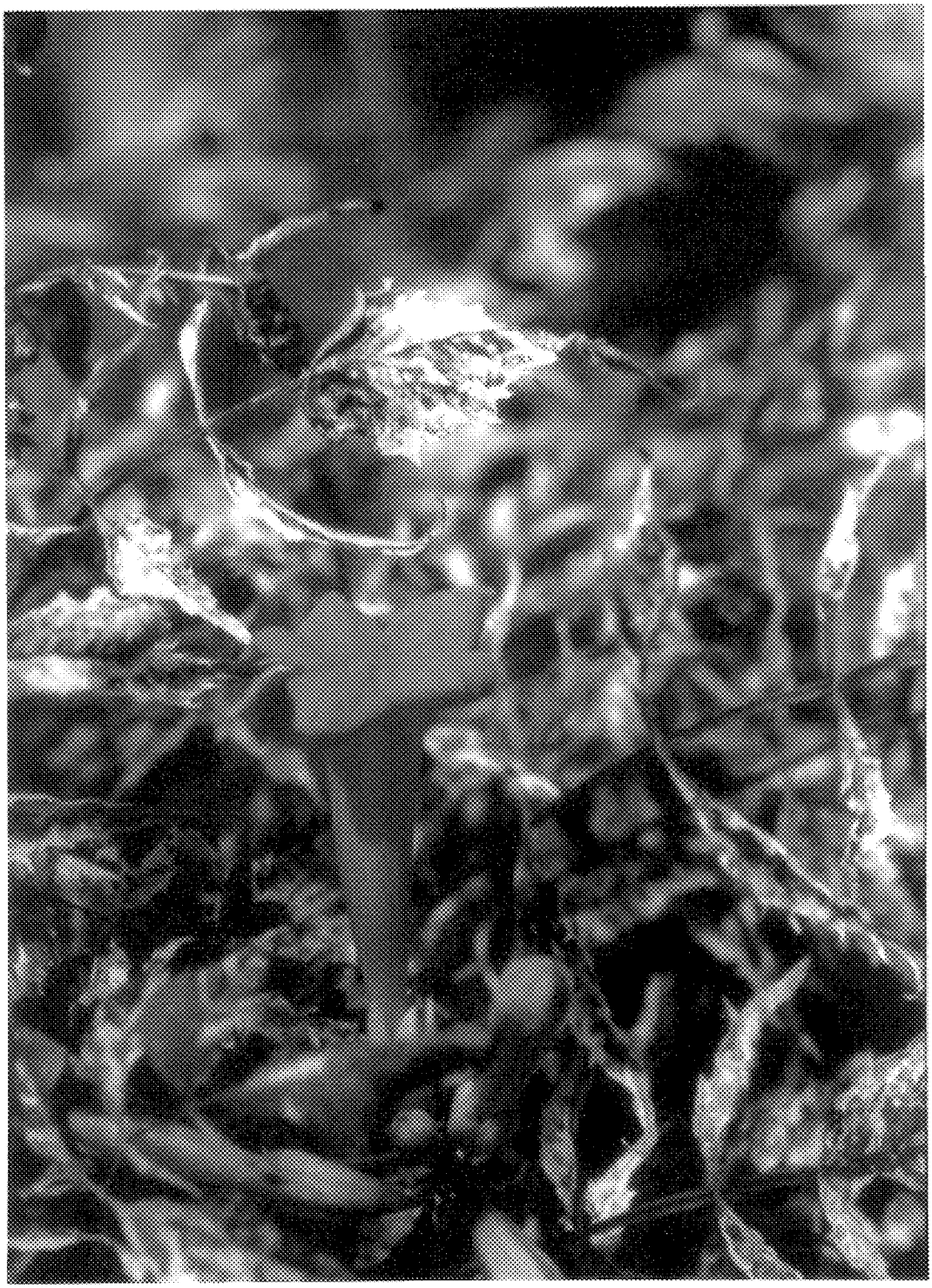
FIG. 5 illustrates a flower of the new variety with the characteristic variegated foliage shown in the background.

'TAKARAZUKA VARIEGATED' has not been observed under all possible environmental, cultural, and light conditions. The following observations and descriptions are of 3-year old plants, in 5-gallon nursery containers, grown in 50% shade in a production nursery setting in Vacaville, Calif., using a soiless media and liquid fertilizer. In this description, color references are to the *Royal Horticultural Society Colour Chart* (1995) and terminology used in the color descriptions herein refers to plate numbers in this color chart. Phenotypic expression may vary with light intensity, cultural, and environmental conditions.

Classification:

*Botanical.—Campsis radicans* (Linnaeus) B.C. Seemmann ex. Bureau (Thunb.) Ser. 'TAKARAZUKA VARIEGATED'.

*Parentage.*—Branch sport in a controlled planting of *Campsis radicans.*

*Propagation.*—By vegetative cuttings.

Plant:

*Size.*—To about 10 m at maturity.

*Branching.*—Lateral Branches: About 3. Typical # Branches: More than 50. Observed # Branches: 8. Branch Size: About 3 m. Branch Diameter: About 7 mm. Branch Coloration: Grey-brown; no spotting.

*Habit.*—Scrambling, twining vine with numerous aerial roots which allow it to climb if supported, or spread along the ground.

*Leaf.*—Arrangement: Opposite, pinnately compound, with a terminal leaflet; about 7 to 13 leaflets. Shape: (Leaflets) Elliptic to ovate-oblong; very irregular in outline and variable. Leaflet Apex: Acuminate to long-acuminate; highly variable in length. Leaflet Base: Cuneate with winged petiolules. Size: Leaflets range from about 2 to 12 cm long, about 1 to 5 cm wide; compound leaves range from about 15 to 40 cm long. Margin: Very irregular in outline, commonly serrated to angularly toothed, sometimes with small lobes and secondary serrations. Texture/Substance Upper Side: Smooth surface; moderately glossy, but very strongly and irregularly bullate overall. Under Side: Barely glossy. Rachis: Sparsely pubescent; from about 7 to 11 cm long from stem to base of terminal leaflet; near Green Group 137B. Petiolules: Variously pubescent; sulcate, winged; about 0.5 to 1.0 cm long on lateral leaflets; often longer, to 3.0 cm on terminal leaflets; near Green Group 137B. Petiole: About 4 to 7 cm from the stem to the first set of leaflets; the base of the petiole is very noticeably swollen on vigorous shoots. Leaf Color: Dark green background color with highly irregular and variable, flecked and mottled white and lighter green variegation. Variegation is most often distributed near the leaf margin but commonly invades the center of the blade in irregular patches. Variegation normally covers less than half the leaflet, and can range from as little as 10% to as much as 60% of the leaf surface. A leaflet's pattern is stable throughout the life of the leaf, but highly variable from leaf to leaf and among plants. Upper Side: Background near Green Group 138C, with some darker areas near Green Group 139A and Greyed-Green Group 189B; variegation near White Group 155C. Under Side: Background near Green Group 137C; variegation near White Group 155C. Venation Pattern: Deeply impressed on upper surface; raised on under surface; midrib and veins pubescent on underside of leaflet. Color Upper Surface: Near Green Group 138C. Under Surface: Near Yellow-Green Group 148C. Internodes: About 10 to 15 cm on vigorous specimens; otherwise highly variable depending on health and vigor of plants.

*Hardiness.*—USDA Zone 4 (30° F. to 20° F.).

*Vigor.*—Extremely vigorous; rapid growth rate.

*Pests/disease.*—None noted.

Infloresence:

*Bloom period.*—Outdoors: Early summer to fall. Greenhouse: May to July.

*Flower form/size.*—Tubular, approximately 7 to 8 cm long from attachment to limb of corolla; the section from attachment to about 2.5 cm from attachment is perfectly tubular, about 0.5 cm in diameter, then gradually flaring to about 2.5 to 3 cm at the limb of the corolla. Flower Arrangement: Between 4 to 12 in a terminal cluster on the current year's wood.

*Calyx.*—Tubular-campanulate; 5 unequal lobes; 2.5 cm long; 5 sharply pointed triangular sepal-lobes, each about 0.5 cm long; the calyx tube is 5-ridged, with ridges aligned with and extending to the tops of the calyx lobes (sepals); calyx tube slightly incurved just past the point of divergence of the lobes, while tips of the lobes are slightly flared. Color: Near Orange-Red Group 32A.

*Corolla.*—Divided into 5 unequal lobes, each 1.5 to 2 cm long; the top 2 lobes are nearly identical, nearly rounded to obovate and strongly recurved; the lower 3 lobes are similar in shape, obovate and slightly longer, with the lateral margins of the lobes folded under. Color Corolla Lobe: Near Orange-Red Group 34A. Corolla Tube: Near Orange-Red Group 32B. Base of Throat: Near Orange-Red Group 25C. Lines on Throat: Near Red Group 32B.

*Fragrance.*—None noted.

*Lastingness of individual blooms.*—Between about 4 to 7 days.

Reproductive organs:

*Stamens.*—4; approximately 3 cm long. Color: Near Yellow-Orange Group 20A.

*Stigma.*—2.

*Pistils.*—1; approximately 5.5 cm long. Color: Near Yellow-Orange Group 18B.

*Pollen color.*—Near Yellow-Orange Group 18B.

*Fruit.*—Type: Bi-valved dehiscent capsule containing numerous flat, winged seeds with glabrous surface. Length: Between about 7 to 12 cm. Diameter: Between about 1 to 1.5 cm. Coloration: Capsule Greyed-Orange Group 164C; seed near Greyed-Orange Group 165A.

I claim:

1. A near plant of *Campsis radicans* of the variety substantially as shown and described.

* * * * *

UNITED STATES PATENT AND TRADEMARK OFFICE

CERTIFICATE OF CORRECTION

PATENT NO. : PP 12,245 P2
DATED : December 4, 2001
INVENTOR(S) : Shinri Wakaiki

It is certified that error appears in the above-identified patent and that said Letters Patent is hereby corrected as shown below:

Title page,
Column 4, in the Claim, replace “near” with -- new --.

Signed and Sealed this

Tenth Day of September, 2002

*Attest:*

*Attesting Officer*

JAMES E. ROGAN
*Director of the United States Patent and Trademark Office*